(12) United States Patent
Halilah

(10) Patent No.: US 7,966,892 B1
(45) Date of Patent: Jun. 28, 2011

(54) IN LINE SAMPLER SEPARATOR

(76) Inventor: Sami O. Halilah, Stafford, TX (US)

( * ) Notice: Subject to any disclaimer, the term of this patent is extended or adjusted under 35 U.S.C. 154(b) by 0 days.

(21) Appl. No.: 12/852,951

(22) Filed: Aug. 9, 2010

(51) Int. Cl.
*G01F 1/74* (2006.01)

(52) U.S. Cl. .................................... 73/861.04

(58) Field of Classification Search ............... 73/861.04, 73/61.45
See application file for complete search history.

(56) References Cited

U.S. PATENT DOCUMENTS

| | | | |
|---|---|---|---|
| 4,429,581 A * | 2/1984 | Furmaga et al. | 73/861.04 |
| 4,596,136 A * | 6/1986 | Zacharias | 73/61.45 |
| 4,596,516 A | 6/1986 | Scott et al. | |
| 4,656,869 A * | 4/1987 | Zacharias | 73/597 |
| 4,776,210 A | 10/1988 | Baillie et al. | |
| 5,212,990 A * | 5/1993 | Stout et al. | 73/861.04 |
| 5,363,696 A | 11/1994 | Cardellini et al. | |
| 6,134,951 A | 10/2000 | Scott et al. | |
| 6,401,529 B1 | 6/2002 | Robison et al. | |
| 6,825,657 B2 | 11/2004 | Kleinberg et al. | |
| 6,870,626 B2 | 3/2005 | Autrey et al. | |
| 7,233,001 B2 | 6/2007 | Lievois et al. | |
| 7,603,916 B2 * | 10/2009 | Gysling | 73/861.42 |

FOREIGN PATENT DOCUMENTS

JP 2002357516 12/2002

\* cited by examiner

*Primary Examiner* — Jewel Thompson
(74) *Attorney, Agent, or Firm* — Richard C. Litman

(57) ABSTRACT

The in-line sampler separator utilizes an improved method of measuring the gas, oil and water components in a fuel material mixture being processed at high pressure in a processing system. A sampling loop obtains mixture samples to be collected in a sampler. The sampler releases the collected sample to a separator tank when a certain volume has been reached. The tank operates at or below a pressure that allows the gas component to be released in gaseous form. The oil and water components separate within the tank, and their respective volumes are determined.

13 Claims, 1 Drawing Sheet

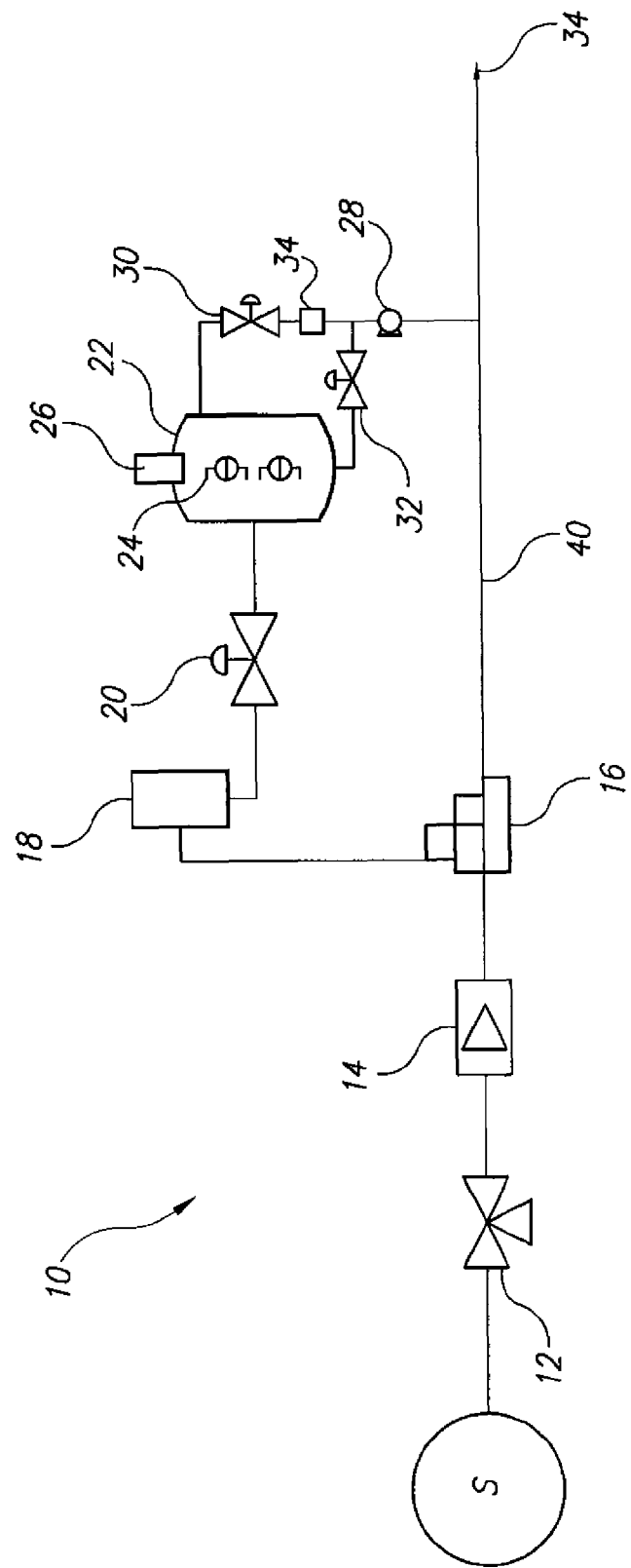

IN LINE SAMPLER SEPARATOR

BACKGROUND OF THE INVENTION

1. Field of the Invention

The present invention relates to a process of measuring product from an oil well, and more particularly to a method of measuring the volume of gas, oil and water passing through a main line within a given period of time.

2. Description of the Related Art

In the oil industry, it is known that the fluid being pumped from an oil well or wells is not pure oil but a mixture or emulsion of gas, oil and water. It is important to monitor the net production of the oil as well as the volume of gas and water that may be produced from the well. Typically, the volume of these components is determined by multiphase and momentum meters, which are expensive and use certain assumptions that may not be accurate. Under line pressure condition, the gas is typically in liquid form and will only partially separate.

Multiphase separator tanks have also been used to determine volume of the mixture. A predetermined volume of mixture is pumped into the tank and allowed to stand for a period of time. The effect of gravity separates the mixture into gas, oil and water due to the different densities of the components. The gas is allowed to escape and the remaining component volumes are measured. However, this system tends to be large, cumbersome and time consuming requiring additional maintenance care and monitoring of the tank.

Another method of measuring is a slipstream method. In this approach, a sampling loop is provided off the path of the main line. A sample of the mixture is drawn from the main line, the volume of the components is measured, and then all products from the mixture are pumped back into the main line. It is a continuous process that leaves the mixture sample at high pressure. Therefore, the gas is still in a liquid state, which leads to inaccuracies in calculating the volume of the gas.

Thus, an in-line sampler separator solving the aforementioned problems is desired.

SUMMARY OF THE INVENTION

The in-line sampler separator improves upon the slipstream sampling method by mixing the oil material to a homogenous mixture, collecting a predetermined amount of samples, releasing the collected sample to a separator tank, monitoring and maintaining the pressure of the tank so that it is at a pressure that promotes separation of the gas in a gaseous state, continuously extracting and measuring the gas, and determining the volume of the oil and water when settled.

These and other features of the present invention will become readily apparent upon further review of the following specification and drawings.

BRIEF DESCRIPTION OF THE DRAWINGS

The sole FIGURE is a schematic flow diagram of the in-line sampler separator according to the present invention.

DETAILED DESCRIPTION OF THE PREFERRED EMBODIMENTS

The present invention relates to an in-line sampler separator and method that measures the component volume in a faster manner due, in part, to the smaller volume than typical being processed for measurement. Moreover, the results are more accurate in a given measurement cycle, e.g., 24-hour period, because the volume of gas in the mixture is more accurately determined.

Referring to the FIGURE, reference number 10 generically represents a fuel material processing system. The fuel material is pumped from a source S to the main line 40, typically 3"-6" diameter, at a high pressure, i.e. line pressure condition. The source may be a well or a plurality of wells. The fuel material is not pure oil but a mixture or emulsion of gas, oil and water. Since the material flows at a high pressure, the gas component is in a liquid state. As noted above, it is necessary to separate each component of the mixture to determine how much, in terms of volume, of each component is flowing from the source. To that end, the fuel material passes through a mixer 12 and a vortex meter 14 to the sampling and separating section of the processing system. The mixer functions to obtain a mixture that is as uniform and homogenous as possible because the fuel material may not always contain gas, oil and water. Sometimes the fluid may be all gas, oil or water depending on various factors from the source such as the unique formation of the well, the pressure inside the well, the depth at which the fuel material is pumped, etc. The vortex meter measures the velocity of the mixture. In place of the vortex meter, any other volumetric measuring device may be employed.

After the material is mixed, discrete amounts of samples are drawn from the main line and processed through a sampling loop 16 operating at a high pressure, i.e., 1200 psi. For instance, three samples are grabbed for each one barrel of fuel material mixture that runs through the line. Each sample can vary in volume, but it is typically one cubic centimeters. Thus, the volume of each sample is known. It is noted that the operating pressure of the sampling loop is the same pressure as in the main line. The samples are then directed to the sampler 18, also operating at high pressure, where they stay until the sampler is full. It usually takes thirty minutes to fill up to the three-gallon capacity of the sampler.

When the sampler is full, sampling is momentarily discontinued, and the contents of the sampler are released to separator tank 22 via a valve 20. Then the sampling process is repeated. The separator tank 22 is closed at both ends, and initially, it is operating at 0 psi. As the high-pressured contents are introduced into the tank, the pressure in the tank begins to increase to about 30 psi. This pressure will continue to increase as more high-pressured contents are introduced therein. The tank preferably has the capacity to hold 1-5 barrels of sampled content. The gas component will immediately separate from the mixture and rise to occupy the uppermost part of the tank. The pressure in the tank is always monitored by a device 26 to maintain the tank at a preselected low pressure, i.e. the pressure that allows the gas to be in a gaseous state. The low pressure insures that the gas component has the proper conditions to be in gaseous form or state rather than liquid. The monitoring device 26 measures temperature and pressure. To assist in maintaining optimum low pressure in the tank, the gas, which has collected towards the top of the tank, is slowly released out of the tank via a valve 30, and the displacement pump 28 reintroduces the released gas into the main line. The volume of this gas flow is always measured and monitored throughout the day, a typical measuring cycle, by a gas meter 34. The oil and water components of the emptied contents accumulate at the bottom of the tank. Over time, the oil component will rise above the water component due to the combined effects of gravity and density of the component materials, i.e. water is heavier than oil. Level indicators or floats 24 are provided in the tank to help indicate the total amount, in volume, of oil and water sampled in a 24-hour period. Other types of dual level indicators may be used in place of floats such as dielectric ultrasonic or radar measuring devices. When measurements are completed, the collected oil and water components are pumped back into the main line to be further processed to a production system 34.

Since the gas, oil and water mixture samples are measured, i.e. the volume of each sample is known, the total amount of each component can be calculated for each 24-hour period, and this amount will represent a proportion of the total amount of mixture that has flown through the main line. In other words, samples taken from the main line are in proportion to the entire flow of the main line. Each sample taken over the course of the day will have varying amounts or percentages of each component. The resultant component volume at the end of the day is an average of all the samples grabbed during that period. Thus, the above method uses representative samples to determine flow rate of the entire line without having to redirect the entire flow, which would be costly. Moreover, the amount of mixture used to measure the volumes of the respective components is smaller than normal. Hence, the measurements may be expeditiously processed.

it is to be understood that the present invention is not limited to the embodiments described above, but encompasses any and all embodiments within the scope of the following claims.

I claim:

1. A method of measuring gas, oil and water component parts in a fuel material processing system comprising the steps of:
   mixing the fuel material from a main line to obtain a uniform mixture;
   measuring flow rate of the uniform mixture;
   obtaining mixture samples of known volume;
   collecting the samples in a sampler up to a given volume;
   releasing the collected samples into a separator tank operating at a given pressure;
   monitoring pressure in the tank to keep the tank pressure low enough to ensure the gas component is in a gaseous state;
   releasing a portion of the gas component as needed to maintain the tank pressure to ensure the gas component goes into a gaseous state;
   measuring a volume of the released gas component; and
   measuring the volume of both the oil and water components at the end of a given measuring cycle.

2. The method of measuring gas, oil and water component parts according to claim 1, further comprising the step of pumping the measured gas, water and oil components back into the main line for further processing.

3. The method of measuring, oil and water component parts according to claim 1, wherein the step of monitoring the tank pressure further comprises the step of providing a temperature and pressure measuring device for notifying release of the gas component when a predetermined limit of temperature and pressure has been reached within the tank.

4. The method of measuring gas, oil and water component parts according to claim 1, wherein the step of measuring the volume of oil and water further comprises the step of providing a dual float assembly, one float assembly indicating volumetric level of the oil component and the other float assembly indicating volumetric level of the water component.

5. The method of measuring gas, oil and water component parts according to claim 1, wherein the step of measuring the volume of oil and water comprises providing a dielectric ultrasonic device to measure the respective volumes.

6. The method of measuring gas, oil and water component parts according to claim 1, wherein the step of measuring the volume of oil and water comprises providing a radar device to measure the respective volumes.

7. The method of measuring gas, oil and water component parts according to claim 1, further comprising the step of providing a vortex meter to measure fluid flow rates.

8. The method of measuring gas, oil and water component parts according to claim 1, wherein the volume of each sampled mixture is about one cubic centimeter.

9. The method of measuring gas, oil and water component parts according to claim 1, wherein the releasing steps are performed by valves.

10. An in-line sampler separator comprising;
    a mixer disposed on a main line for mixing fuel material into a uniform mixture;
    a flow rate meter for measuring the flow rate of the uniform mixture downstream of the mixer along the main line;
    a sampling loop for obtaining a predetermined volume of discreet samples of the uniform mixture, the sampling loop being disposed downstream of the vortex meter along the main line;
    a sampler operatively connected to the sampling loop for collecting the uniform mixture samples up to a given volume;
    a separator tank for receiving the given volume of uniform mixture samples from the sampler and separating the uniform mixture into gas, oil and water components, the separator tank being disposed adjacent the sampler and having a given pressure;
    a first valve mechanism for releasing the uniform mixture samples from the sampler to the separator tank when the given volume has been reached;
    a monitoring assembly operatively attached to the separator tank to maintain pressure in the tan low enough to ensure the gas component is in a gaseous state;
    a second valve mechanism for releasing the gas component towards the main line to maintain the tank pressure low enough to ensure a gaseous state;
    a gas metering device for measuring a volume of the released gas component;
    a fluid measuring device operatively connected to the separator tank for measuring the volume of both the oil and water components at the end of a given measuring cycle;
    a third valve mechanism for releasing the oil and water components towards the main line at the end of the given measuring cycle; and
    a pump for pumping gas, oil and water components back into the main line for further processing.

11. The in-line sampler separator according to claim 10, wherein the monitoring assembly comprises a temperature and pressure measuring device to notify release of the gas component when a predetermined limit of temperature and pressure has been reached within the tank.

12. The in-line sampler separator according to claim 10, wherein the fluid measuring device is selected from the group of dual float assemblies, dielectric ultrasonic devices, and radar devices.

13. The in-line sampler separator according to claim 10, wherein the predetermined volume of each sampled mixture is about one cubic centimeter.

* * * * *